United States Patent
Miljkovic

(10) Patent No.: US 8,852,660 B2
(45) Date of Patent: Oct. 7, 2014

(54) COMPOSITIONS AND METHODS FOR PRODUCING STABLE NEGATIVE OXIDATION REDUCTION POTENTIAL IN CONSUMABLE MATERIALS

(76) Inventor: Dusan Miljkovic, San Diego, CA (US)

( * ) Notice: Subject to any disclaimer, the term of this patent is extended or adjusted under 35 U.S.C. 154(b) by 0 days.

(21) Appl. No.: 12/790,654

(22) Filed: May 28, 2010

(65) Prior Publication Data

US 2010/0316776 A1      Dec. 16, 2010

Related U.S. Application Data

(60) Provisional application No. 61/187,381, filed on Jun. 16, 2009.

(51) Int. Cl.

| | | |
|---|---|---|
| A23C 9/14 | (2006.01) | |
| A23L 1/304 | (2006.01) | |
| A23L 3/3526 | (2006.01) | |
| A23L 3/349 | (2006.01) | |
| A23L 3/358 | (2006.01) | |
| A23L 2/52 | (2006.01) | |
| C02F 1/70 | (2006.01) | |
| A23L 1/30 | (2006.01) | |
| C02F 1/00 | (2006.01) | |
| C02F 1/68 | (2006.01) | |
| C02F 1/52 | (2006.01) | |

(52) U.S. Cl.
CPC .............. C02F 1/70 (2013.01); A23L 1/3045 (2013.01); *C02F 1/001* (2013.01); A23L 3/3526 (2013.01); *C02F 1/688* (2013.01); A23L 3/349 (2013.01); A23L 3/358 (2013.01); *C02F 1/52* (2013.01); *A23V 2002/00* (2013.01); A23L 2/52 (2013.01); A23L 1/304 (2013.01); *C02F 1/705* (2013.01); A23L 1/30 (2013.01)
USPC ............... 426/271; 209/5; 424/602; 204/554; 210/695; 426/74; 426/636

(58) Field of Classification Search
USPC ......................................................... 426/649
See application file for complete search history.

(56) References Cited

U.S. PATENT DOCUMENTS

| | | | | |
|---|---|---|---|---|
| 2,403,010 | A | | 7/1946 | McHan |
| 2,404,367 | A | * | 7/1946 | Durant et al. ................. 210/685 |
| 2,437,815 | A | * | 3/1948 | Hansgirg ........................ 75/599 |
| 4,814,195 | A | * | 3/1989 | Yokoyama et al. ........... 426/633 |
| 5,407,696 | A | * | 4/1995 | Hagiwara et al. ............. 426/636 |
| 5,612,061 | A | * | 3/1997 | Rabkin .......................... 424/602 |
| 5,950,435 | A | | 9/1999 | Kaizuka |
| 5,951,839 | A | * | 9/1999 | Reznik .......................... 204/554 |
| 6,692,788 | B1 | | 2/2004 | Mottram et al. |
| 6,703,056 | B2 | * | 3/2004 | Mehansho et al. .............. 426/74 |
| 6,793,883 | B2 | * | 9/2004 | Andresen et al. ................. 422/7 |
| 7,189,330 | B2 | | 3/2007 | Hayashi et al. |
| 2002/0034543 | A1 | * | 3/2002 | Kirschner et al. ............ 424/465 |
| 2002/0158018 | A1 | * | 10/2002 | Abramowitz et al. ........ 210/639 |
| 2003/0059514 | A1 | * | 3/2003 | Villagran et al. ............. 426/590 |
| 2005/0154064 | A1 | * | 7/2005 | Piomelli et al. ............... 514/625 |
| 2005/0159598 | A1 | * | 7/2005 | Ingold et al. .................. 540/603 |
| 2005/0170011 | A1 | * | 8/2005 | Yanagihara et al. .......... 424/600 |
| 2006/0008908 | A1 | | 1/2006 | Giles |
| 2006/0266381 | A1 | * | 11/2006 | Doherty et al. .............. 134/25.2 |
| 2006/0275474 | A1 | | 12/2006 | Bagley |
| 2008/0069779 | A1 | | 3/2008 | Tamarkin et al. |
| 2008/0260922 | A1 | | 10/2008 | Kirkpatrick et al. |
| 2010/0196577 | A1 | * | 8/2010 | Rivera et al. ................. 426/590 |

FOREIGN PATENT DOCUMENTS

| | | |
|---|---|---|
| EP | 0 889 007 | 7/1999 |
| EP | 2027779 | 2/2009 |
| WO | WO 2006/099237 | 9/2006 |

OTHER PUBLICATIONS

Wang: Reduction of Halogenated Hydrocarbons with Magnesium Hydrolysis Process; Bull. Environ. Contam. Toxicol. (1990); 1990 Springer-Verlag New York Inc.*
SIS: Scientific Instrument Services; printed May 2012.*
Duanereade: http://www.duanereade.com/health/NaturalHealthProductFactsheet.aspx?id=55; printed online Nov. 2013.*
The Center of Young Woman's Health: http://web.archive.org/web/20080328141003/http://www.youngwomenshealth.org/menstrual7.html; published online Mar. 2008.*
http://www.nlm.nih.gov/medlineplus/druginfo/meds/a601073.html; printed Apr. 7, 2014.*

* cited by examiner

*Primary Examiner* — Patricia George
(74) *Attorney, Agent, or Firm* — Timothy M. Brown, Esq.

(57) ABSTRACT

Compositions of reducing agents and carriers for producing a stable negative oxidation reduction potential in consumable materials are disclosed and claimed. Compositions of the invention find use in enhancing the hydration and anti-oxidant value of consumable materials such as foods, beverages and cosmetics, for example. Compositions of the invention also find use in water treatment, agricultural and scientific research applications. Methods for using and making the compositions are also within the scope of the invention.

4 Claims, No Drawings

COMPOSITIONS AND METHODS FOR PRODUCING STABLE NEGATIVE OXIDATION REDUCTION POTENTIAL IN CONSUMABLE MATERIALS

CROSS-REFERENCE TO RELATED APPLICATIONS

This application claims priority from U.S. Provisional Application Ser. No. 61/187,381, filed Jun. 16, 2009, the contents of which are incorporated by reference in their entirety.

FIELD OF THE INVENTION

The invention relates to compositions for producing a negative oxidation reduction potential in materials for use in retail, agricultural, health care, cosmetic, water treatment and scientific research applications.

BACKGROUND

Exposing living organisms to negative oxidation reduction potential conditions provides a number of health benefits. For example, beneficial anaerobic bacteria in the human digestive tract grow better under reducing conditions (Curr. Tr. Options in Gastr. 2007, 10: 312-321). Evidence suggests that negative oxidation reduction potential ("NORP" or "negative ORP") may also provide benefits in modulating inflammatory responses in the treatment of colitis and inflammatory bowel disease (Aliment Pharmacol Ther 2006, 24:701-714).

NORP conditions are also believed to provide antioxidant benefits similar to vitamins and enzymes such as superoxide dismutase, catalase and glutathione peroxidase. Thus, NORP materials are considered to function as scavengers of reactive oxygen species including free radicals (J. of App. Electrochem. 2001 31: 1307-1313). Negative ORP water is reported to provide benefits in treating diabetes and metabolic syndrome (Cytotech. 2002, 40: 139-142; Nutr. Res. 2008; 28:137-143).

Not surprisingly, commercial devices have been developed for producing NORP drinking water. Water electrolyzers, such as those disclosed in U.S. Pat. No. 6,623,615 for example, use an electric current to produce alkaline NORP drinking water in the home. These devices have two drawbacks. First, the NORP produced by electrolyzers is unstable and water treated with these devices loses its NORP over time. Electrolytically treated drinking water must therefore be consumed soon after it is treated in order to obtain its NORP benefits. Second, electrolytic devices are impractical for portable use due to their size and need for an electrical power source and connection to a water tap.

Another means for producing reduced drinking water is the subject of U.S. Pat. No. 7,189,330 to Hayashi et al. This document describes a device comprising grains of elemental magnesium and silver which are encased in a ceramic housing in the form of a stick. In practice, these sticks are placed in drinking water for the production of 'hydrogen rich' NORP drinking water.

Applicant observed that the Hayashi et al. device suffers from a number of limitations. First, drinking water treated with the Hayashi et al. device only achieved a NORP of about −50 mV to −100 mV. Second, Applicant observed that the Hayashi et al. device took several hours to produce this slightly increased NORP. The third disadvantage that Applicant observed was that the NORP produced by the Hayashi et al. device was unstable as the treated water returned to its initial oxidation reduction state shortly after the device was removed. Fourth, Applicant observed that the Hayashi et al. device has a limited useful life due to the oxidation of the device's magnesium and silver grains. Fifth, the Hayashi et al. device has a certain potential for microbial cross-contamination since it is designed for multiple uses and might be used to treat the drinking water of different individuals.

Applicant noted that what was needed in the art therefore was a portable means for quickly and efficiently producing a strong, stable NORP in drinking water and other consumable materials almost without any potential for microbial contamination.

SUMMARY OF THE INVENTION

Applicant's invention overcomes the shortcomings of known methods and devices for producing beneficial NORP by providing safe, stabilized additives for use in retail, agricultural, health care, cosmetic, wastewater treatment and scientific research applications.

In one aspect, the invention provides an additive for producing a NORP in a consumable material, wherein the additive comprises a mixture of at least one reducing agent, and at least one carrier, wherein the carrier is water soluble and non-toxic.

In another aspect, the invention provides an additive for producing a NORP in a consumable material, wherein the additive comprises a mixture of at least one reducing agent, and at least one carrier, wherein the additive produces a negative oxidation reduction potential of between about −200 and −800 mV in the consumable material.

In another aspect, the invention provides an additive for producing a NORP in a consumable material, wherein the mixture comprises (a) a reducing agent that is selected from the group consisting of an organic reducing agent, an inorganic reducing agent, and combinations thereof, and (b) at least one carrier selected from the group consisting of a base, a saccharide, an ascorbate analog, EDTA analog, and combinations thereof.

In another aspect, the invention provides an additive for producing a NORP in a consumable material, wherein the mixture comprises (a) a reducing agent comprising particles of an elemental metal selected from the group consisting of magnesium, calcium, zinc, iron, copper, cobalt, manganese, and combinations thereof.

In another aspect, the invention comprises a method for producing a NORP in a consumable material comprising providing a consumable material, providing an additive comprising at least one reducing agent and at least one carrier, and contacting the consumable material with the additive under conditions suitable to produce a NORP in the consumable material, wherein the consumable material is a food, beverage, food substitute, dietary and nutritional supplement, animal feed, material for horticultural use, or material for scientific research.

In another aspect, the invention provides a composition for treating waste water, wherein the composition comprises a mixture of at least one reducing agent, and at least one carrier.

In another aspect, the invention provides a method for treating wastewater, wherein the method comprises (a) providing wastewater, (b) producing a NORP in the wastewater by contacting the wastewater with an additive comprising at least one reducing agent and at least one carrier, wherein producing a NORP in the wastewater causes contaminants in the wastewater to precipitate, and (c) removing the precipitated contaminants from the wastewater.

DEFINITIONS

As used herein, the term "additive," or "reducing additive" refers to a mixture comprising at least one reducing agent and at least one carrier, wherein the additive produces a negative oxidation reduction potential in a material when the additive is contacted with an aqueous consumable material.

As used herein, the term "consumable material" refers to any material that provides nourishment for the growth or metabolism of a living organism.

As used herein, the term "aqueous consumable material" refers to a consumable material that comprises water in a sufficient quantity to achieve an increase in negative oxidation reduction potential when the material is contacted with a reducing agent. The term "aqueous consumable material" includes, but is in no way limited to, water which is free of other substances.

As used herein, the term "biological value" refers to reduction potential (reduction capacity), hydration potential, and/or anti-oxidant potential obtained by a living organism through the ingestion of a consumable material. An "increase in biological value" refers to a measurable increase in the biological value, of a consumable material as a result of the consumable material being contacted with an additive as disclosed herein.

As used herein, the term "treat," or "treating," means contacting (e.g. combining) a material (e.g. consumable material) with an additive, wherein such contacting produces a measurable increase in the negative oxidation reduction potential of the material. The term "treating" includes, but is not limited to, increasing the biological value of a consumable material as a result of being contacted with an additive as disclosed herein.

As used herein, the term "non-toxic" means materials which are safe for ingestion by a living organism, including plants and animals, preferably mammals, and more, preferably humans.

As used herein, the terms "reducing agent," and "reductant," refer to a substance that is readily oxidized by simultaneously reducing another substance. Reducing agents include electron donors, hydride donors and hydrogen donors.

The terms "oxidizing agent," and "oxidant" are used interchangeably herein to refer to either a) a chemical compound that readily transfers oxygen atoms, or b) a substance that gains electrons in a redox chemical reaction. In both cases, the oxidizing agent becomes reduced in the process.

As used herein, the terms "shift in oxidation reduction potential," "shift in ORP," "oxidation reduction potential shift," and "ORP shift" are used to refer to a measurable change in the oxidation reduction potential of a material. For example, a change from +200 mV to −200 mV in a material is a 400 mV shift in oxidation reduction potential.

As used herein, the term "target NORP" refers to a negative oxidation reduction potential, or range of negative oxidation reduction potential, that is desired in a selected material (e.g. consumable material).

As used herein, the term "producing a negative oxidation reduction potential" or "producing a NORP" refers to increasing or maintaining the negative oxidation reduction potential of a material (e.g. consumable material) by contacting the material with an additive as disclosed herein. An increase in negative oxidation reduction potential refers to a measurable net increase in the negative oxidation reduction potential of a material that results from the material being contacted with a reducing agent (e.g. additive) relative to the negative oxidation reduction potential of the material in the absence of contact with the reducing agent. Similarly, maintaining the negative oxidation reduction potential of a material refers to the ability of an agent (e.g. additive or reducing agent) to prevent or inhibit the loss of negative oxidation reduction potential in a material (e.g. consumable material) relative to the loss of oxidation reduction potential that results in the absence of such agent.

As used herein, the term "aqueous solution," "aqueous environment," or "aqueous material," refers to any material (e.g. aqueous consumable material) that contains water in a sufficient quantity to allow the material to develop a negative oxidation reduction potential when the material is contacted with a reducing agent (e.g. additive). Aqueous materials include, but are not limited to, liquids (e.g. viscous liquids), gels, sols and pastes.

As used herein, the term "base" refers to any chemical compound or material that, when dissolved in water, gives a solution with a hydrogen ion activity lower than that of pure water (i.e. a pH higher than 7.0 at standard conditions). Bases include, but are not limited to, alkalis and organic bases (e.g. compounds containing an amino group).

As used herein, the term "alkaline," or "basic," refers to a hydrogen ion activity lower than that of pure water (i.e. a pH higher than 7.0 at standard conditions).

As used herein, the term "alkali," or "alkaline agent," refers to a basic, ionic salt, oxides or hydroxides of an alkali metal or an alkaline earth metal.

As used herein, the term "carrier" refers to any substance that may be formulated with a reducing agent to produce a NORP in a consumable material as disclosed herein. Such carriers may be liquid, powder, gel, sol or paste in form. Carriers of the invention include, but are in no way limited to, (i) bases, (ii) buffers, (iii) inert materials for adding volume to the additives of the invention (e.g. excipients, bulking agents and binders), (iv) compounds that, when combined with a reducing agent, inhibit or prevent the oxidation of the reducing agent by environmental conditions such as exposure to atmospheric moisture, (v) materials that help maintain the negative oxidation reduction potential of a reduced consumable material, and (vi) combinations thereof. Carriers may be soluble or insoluble in water.

As used herein, the term "purified," or "pure," means that a material is at least 95% (by dry weight or molar ratio) free of other materials.

DETAILED DESCRIPTION

The invention generally relates to additives for quickly and efficiently producing a stable NORP in materials for use in retail, agricultural, health care, cosmetic, water treatment and scientific research applications. The invention includes methods of using such additives to increase the nutrient and health benefits of consumable materials. The invention also relates to methods for making the additives of the invention.

In some aspects, the additives of the invention comprise a mixture of a reducing agent and a carrier. Such mixtures may be formulated with at least one reducing agent and at least one carrier. The additives of the invention may be formulated with inorganic reducing agents, organic reducing agents, or a combination thereof.

The invention may be practiced with any inorganic reducing agent capable of producing a negative ORP when contacted with an aqueous material as disclosed herein. Suitable inorganic reducing agents may comprise, for example, elemental metals. Such elemental metals include, but are not limited to, magnesium (Mg), calcium (Ca), zinc (Zn), iron (Fe), copper (Cu), cobalt (Co), manganese (Mn), and combinations thereof. In some aspects, the additives are formulated for reducing materials not intended for animal or human consumption. For example, additives may be formulated for use in wastewater and horticultural applications as described herein. Such additives may comprise reducing agents including, but not limited to, hydrazines (e.g. hydrazine salts), borohydrides [e.g. $LiBH_4$, $NaBH_4$, $NaBH_3CN$, $KBH_4$], sulphites, and combinations thereof. These reducing agents may be used alone, or in combination with one or more of the elemental metals called out above.

The additives of the invention may be formulated with organic reducing agents. Such reducing agents include any organic reducing agent that produces a NORP when contacted with an aqueous material (e.g. consumable material) as described herein. Additives of the invention may be formulated with organic derivatives of hydrazine and/or dihydropyridines. Some suitable organic reducing agents for use with the invention include, but are not limited to, amino-guanidine, dihydro-pyrrol derivatives, dihydro-furan derivatives, dihydro-pyridine derivatives, 1,4-dihydro-pyridine derivative (dihydro-trigonelline—DHT), and combinations thereof.

As noted above, the additives of the invention are formulated with one or more carriers. Carriers for use with the invention preferably do not cause or contribute to the oxidation of the reducing agent(s) when reducing agent(s) and carrier(s) are combined with one another. One skilled in the art will appreciate that the selection of carriers (as well as reducing agents) will depend upon the particular application to which the additive will be applied. For example, a soluble or non-soluble carrier may be desired. Carriers for use with the invention include, but are in no way limited to, bases, saccharides, ascorbate analogs, EDTA, EDTA analogs, and combinations thereof.

Carriers for use with the invention include alkalis. The term "alkali," or "alkaline carrier," as used herein, refers to a basic, ionic salt, oxide or hydroxide of an alkali metal or alkaline earth metal. Formulating the additives of the invention with an alkaline carrier permits them to adjust the pH of a material (e.g. consumable material) to which they are added, while simultaneously producing a NORP. Alkalis for use with the invention may include, but are not limited to, sodium bicarbonate, potassium bicarbonate, sodium carbonate, potassium carbonate, magnesium carbonate, magnesium oxide, calcium carbonate, and combinations thereof.

The invention further contemplates additives comprising organic bases. Suitable organic bases for use with the invention include, but are not limited to amines, deprotonated amino acids, and combinations thereof.

In some aspects, the additives of the invention are formulated with one or more saccharide (e.g. carbohydrate) carriers. As with other forms of carrier, saccharide carriers should not oxidize the reducing agent(s) or negatively affect the ability of the reducing agent(s) to produce a negative ORP in a material (e.g. consumable material). Saccharides for use with the invention include, but are not limited to, monosaccharides, disaccharides, oligosaccharides, polysaccharides, sugar alcohols, and combinations thereof. Some sugars for use with the invention include, but are not limited to, fructose, glucose, mannose, sorbose, xylose, maltose, lactose, sucrose, inulin, dextran, and combinations thereof. Some non-limiting examples of suitable sugar alcohols include mannitol, sorbitol, inositol, dulcitol, xylitol, arabitol, and combinations thereof. The invention further contemplates formulating reducing agents with carriers comprising artificial sweeteners. Suitable artificial sweeteners include, but not limited to, sucralose, aspartame, saccharin, acesulfame K, and combinations thereof.

In aspects of the invention, additives are formulated by combining reducing agents with a sufficient amount of carrier(s) to stabilize the reducing potential of the reducing agents. That is, combining reducing agents with a sufficient quantity of a carrier may be used to prevent or inhibit the oxidation of the additive before the additive can be used to treat a material (e.g. consumable material) as disclosed herein. For example, reducing agents may be combined with a sufficient amount of one or more carriers to prevent the reducing agent from being oxidized by exposure to atmospheric oxygen. Similarly, strongly reducing agents may be made safe for use in producing a NORP through their combination with a sufficient quantity of carrier. For example, the risk of the uncontrolled combustion of finely divided magnesium (e.g. particles below −35 mesh), may be eliminated by combining the magnesium with a sufficient quantity of a carrier. One non-limiting example of such a formulation comprises magnesium particles (between about 37 to 500 microns) combined with potassium bicarbonate in weight ratio of between about 1:4 and 1:50 (magnesium:potassium bicarbonate).

Reducing agents may be stabilized by formulating them with a proportionately greater amount of a carrier. Some suitable ratios for stabilizing reducing agents include, but are not limited to, ratios between about 1:4 and about 1:50 (reducing agent:carrier) by weight or molar ratio. One skilled in the art will appreciate that the additives of the invention may be formulated with any reducing agent to carrier ratio that inhibits or prevents the oxidation of the additive under atmospheric conditions, for example.

Carriers for combining with reducing agents may be selected for their ability to enhance the capacity of reducing agents to produce and/or maintain a negative ORP in materials (e.g. consumable materials). Such carriers may be referred to herein as "NORP-enhancing carriers." NORP-enhancing carriers allow the reducing agent(s) with which they are formulated to produce and/or maintain a greater NORP in a consumable material than in the absence of such NORP-enhancing carriers. NORP-enhancing carriers may also increase the period of time during which a consumable material maintains its NORP. For example, magnesium complexing agents may be used to increase the ability of magnesium to produce and maintain a negative ORP in a consumable material. Such magnesium complexing agents include, but are not limited to, ascorbates, EDTA, EDTA-like ligands (e.g. EDTA analogs), citrates, malates, tartarates, monosaccharides, oligosaccharides (e.g. mannitol and inulin), and combinations thereof.

Carriers for use with the invention further include, but are not limited to, sodium citrate, dicalcium phosphate, fillers or extenders (such as starches, lactose, sucrose, glucose, mannitol, and silicic acid), binders (such as, for example, carboxymethyl-cellulose, alginates, gelatin, polyvinylpyrrolidinone, sucrose, xanthan gum, aloe gel, and acacia), disintegrating agents (such as agar-agar, calcium carbonate, potato or tapioca starch, alginic acid, silicates, and sodium carbonate), buffering agents and combinations thereof.

One aspect of the invention relates to the ratio of the reducing agents and carriers that are used to formulate the additives (i.e. mixtures) of the invention. The additives of invention may be formulated using any reducing agent to carrier ratio that permits the additive to produce a desired NORP and/or pH in a material (e.g. consumable material. One skilled in the art will appreciate that the relative amounts of reducing agents and carriers used will depend on many variables, including, but not limited to, the strength of the reducing agent(s), the chemical properties of the carrier, the desired level of NORP (i.e. target NORP), the desired concentration of the reducing agent in the additive, the starting level of NORP in the consumable material to be reduced, the pH desired in the consumable material to be treated, and/or the amount of carrier needed to stabilize the reducing agent(s).

The additives of the invention may be formulated to achieve a desired level of NORP in an object consumable material. As used herein, the term "object consumable material" refers to a consumable material that is intended to be treated (i.e. reduced) with an additive of the invention. Similarly, an object consumable material may be a reference material that is used to define a specific reduction potential for the additives of the invention. Distilled water and reverse-osmosis (RO) water are non-limiting examples of such a reference material. For example, and in no way limiting, an additive may be formulated to produce a target NORP of between about −200 to −800 my at a concentration of between about 0.2-0.5 grams/L of distilled water. One skilled in the art will appreciate that the proportions and amounts of carriers and reducing agents will vary according to the particular reducing agent that is selected and the negative shift in ORP desired.

In some aspects of the invention, additives are formulated for achieving a target NORP in foods and beverages for human consumption. Without being limited to any particular range or value of NORP, additives of the invention may be formulated to produce a target NORP of between about −200 mV and −800 mV (or at least −200 mV) in a consumable material. In some embodiments, the additives of the invention are formulated to produce a negative ORP shift of about −600 mV. The desired level of NORP shift may depend on the natural NORP value of the object consumable material (e.g. food or beverage) and the level of NORP desired. For example, an object consumable material may have a natural (i.e. initial or resting) ORP of +100 mV. If the target NORP for the object consumable material is about −600 mV, the additive will be formulated to produce a negative NORP shift of about −700 mV. The formulation for such additive may depend upon the volume of the object consumable material to be treated and the amount of additive that is to be combined with the consumable material. For example, the additive may be formulated to produce a shift of −700 mV in a liter of beverage using a selected amount of additive. One skilled in the art will appreciate that a target NORP may be achieved by obtaining an average of the natural ORP for an object consumable material, and adjusting the concentration of the reducing agent in the additive, or adjusting the amount of additive that is contacted with a selected volume of the object consumable material.

It is also contemplated that an additive for producing an NORP in foods and beverages may be formulated using a reducing agent and a carrier comprising a base. Such additives may formulated (and used) to achieve a target NORP of between about −200 mV and −800 mV (or at least −200 mV), and a pH of between about 8 and 10.

In some aspects of the invention, additives are formulated with at least one elemental metal and at least one carrier, wherein the carrier(s) are in a proportionately greater amount (by weight or molar ratio). Such ratios might include, for example, an elemental metal to carrier ratio from between about 1:4, to about 1:50. One skilled in the art will appreciate that the invention may be practiced with any reducing agent to carrier ratio that permits the additives of the invention to reduce a consumable material as disclosed herein. One non-limiting example of an additive formulation of the invention includes a mixture comprising magnesium particles and at least one carrier (e.g. saccharide, base, EDTA, ascorbate analog, or combinations thereof), wherein the magnesium and carrier(s) are present in a ratio of between about 1:4 and 1:50 (by molar ratio or weight) respectively.

In some embodiments, the additives of the invention are formulated using reducing agents in the form of particles (e.g. a powder). For example, the additives may comprise particles including, but not limited to, organic reducing agents, elemental metals, and combinations thereof. The size of particles used may depend on the strength of the reducing agent and the length of time desired to achieve a target NORP in a material (e.g. consumable material). In general terms, and without being limited to any particular theory, smaller particle sizes increase the surface area of the reducing agents thereby shortening the time needed to achieve a target NORP, and increasing the final NORP value of the material. Suitable particle sizes for practicing the invention include, but are not limited to, particles ranging between about −400 and −35 mesh (i.e. around 37 to 500 microns). In an aspect of the invention, additives are formulated using magnesium particles of about 45 microns. The particles may comprise particles of a uniform size, or a mixture of different sized particles. While specific ranges of particle sizes are called out here, the invention contemplates the use of any particle size (or sizes) that permits the additives of the invention to produce a NORP in a consumable material as disclosed herein.

The additives of the invention may take on a number of different formats, including, but not limited to, powders, liquids, gels, sols, and slurries. In some aspects of the invention, the additives assume a dry formulation (i.e. a dry additive). Such dry forms include, but are not limited to, capsules, tablets, effervescent tablets which may be prepared for combining with a material (e.g. consumable material). Dry additives may also be formulated as compressed powdered beads or a powdered aerosol. Dry additives may further be formulated as effervescent compositions using known formulations that include sodium bicarbonate, citric acid, and the like. The additives of the invention may be packaged to resist environmental oxidation. This may be accomplished using airtight packaging such as foil pouches (e.g. stick-packs) or plastic containers, for example.

The additives of the invention find use in any application where it is desirable to provide reductive properties to a material in a quick and efficient manner through the use of an additive. Such applications include, but are not limited to, retail, agricultural, healthcare, cosmetic, water treatment and scientific research applications.

In some aspects of the invention, additives are used to produce a negative ORP in consumable materials, including, but not limited to, foods, beverages, confectionary, desserts, food substitutes and dietary and nutritional supplements. As noted above, ingesting food and beverages that have a high negative ORP (e.g. an ORP of between about −200 and −800 mV) has a number of health benefits. The additives of the invention may be used to produce (e.g. increase) the NORP of beverages for human consumption such as, for example, water (e.g. spring, well, glacial, distilled, RO and filtered water), juices, coffee drinks, tea drinks, flavored beverages (e.g. malts, artificially and naturally flavored fruit drinks, flavored water and the like), nutrient (e.g. mineral) water, energy drinks, hydrating electrolyte sports drinks, milk, and combinations thereof. Suitable formats for producing a NORP in beverages include, but are not limited to, water soluble tablets and powders, including effervescent powders and tablets. Such effervescent and non-effervescent powders may be packaged in sachets.

The additives of the invention may also be used to increase the health benefits of any ingestible food. For example, the additives of the invention may be used to increase the NORP of dairy products, fruits, grain-based foods, condiments, sweeteners (e.g. sugar and sugar substitutes), spices, sauces, and combinations thereof. Additives of the invention may also be used to produce a NORP in food substitutes, dietary and nutritional supplements and drink mixes. For example, the additives of the invention may be combined with protein powders, vitamin and mineral supplements (in pill, capsule, extract and drink mix form), food and snack bars, herbal supplements, cleanses and meal replacement shakes. Additives used in this capacity may come in the prepared (e.g. packaged) food, or the additives may be added to the food immediately before consumption.

In aspects of the invention, additives are combined with materials (e.g. consumable materials) which do not contain enough water for the additive to produce a NORP in the consumable material. This would apply to any dry consumable material such as, for example, dry foods, freeze-dried foods, drink mixes, dry cosmetics (e.g. powders, sticks and deodorants), flour, corn starch, prepared mixes for producing baked goods (e.g. pancake, bread and cake mixes), and nutritional supplements (e.g. protein powders and drink mixes). Although contacting such dry consumable materials with an additive may not produce a NORP due to the absence of water, such treated foods are provided with the potential to produce an NORP once contacted with water. Thus, the phrase "producing a NORP" includes providing a dry material with the potential to achieve a NORP when contacted with water.

The additives of the invention also find use in producing a NORP in cosmetic products. As used herein, the terms "cosmetic products," and "cosmetics," refer to any product applied to the skin or hair for the purpose of beautifying, preserving, restoring, enhancing, cleansing or improving the appearance of the skin or hair. Such cosmetics include, but are in no way limited to, makeup, soaps, shampoos, conditioners, hair tonics, washes, exfoliants, lotions, sunscreens, creams, milks, oils, essences, perfumes, extracts, mouthwashes, deodorants, antiperspirants, shaving creams, shaving lotions, shaving gels, and after shave. Additives used in this capacity may be pre-formulated in the prepared (e.g. packaged) cosmetic product, or the additives may be added to the cosmetic immediately before use. For example, an additive may be added to a wash or soap immediately before washing and/or exfoliating the skin so as to preserve the beneficial reducing potential of the additive until just prior to use. The additives of the invention may also find use in increasing the NORP in feminine hygiene products.

In an aspect of the invention, additives are used to produce a NORP in cosmetics to so as to provide the cosmetics with strong anti-oxidant properties. Cosmetics with anti-oxidant NORP have a number of benefits including, for example, neutralizing oxidative stress, anti-aging effects and improved hydration. Thus, NORP cosmetics may be used to improve the health and appearance of the skin. As used herein, the term "NORP cosmetics" refers to cosmetics which have been reduced, or dry cosmetics that have achieved the potential to reduce an aqueous environment, through contact (i.e. mixing) with an additive of the invention. Dry NORP cosmetics applied to the skin may produce a beneficial NORP as the skin emits water through perspiration or diffusion to provide an aqueous environment. NORP cosmetics may be used for anti-aging effects, improving skin moisture and turgor, diminishing lines and wrinkles, diminishing sun spots, treating sunburn and skin allergies, treating chemical and thermal burns, and treating insect bites and injuries resulting from contact with poisonous plants.

Additives of the invention may be formulated using a reducing agent in combination with a carrier comprising a base. Such additives may be formulated to achieve a target NORP of between about −200 mV and −800 mV (or at least −200 mV), and a pH of between about 8 and 10.

The additives of the invention may also find use in pharmaceutical and health care applications. For example, the additives of the invention may be used to increase the NORP in pharmaceutical grade aqueous solutions such as, for example, eye drops, nasal drops, ear drops, sublingual drops, inhalants, intravenous solutions, and orally administered medications (e.g. cough syrups). The additives of the invention may also be used in the formulation of topical medications, including, but not limited to, antibiotics, anti-inflammatory medications and antifungal agents. For example, such topical formulations may be applied alone, or in the form of an impregnated bandage or transdermal patch. As with foods, beverages and cosmetics, topical formulations may be pre-formulated with the additives of the invention, or the additives may be applied to the topical medication immediately before use.

The additives of the invention find use in agricultural applications. For example, additives may be produced in bulk for treating drinking water for livestock. The additives of the invention may also be used to produce an NORP (and/or target pH) in drinking water for consumption by animals including, but not limited to, cattle, horses, pigs, sheep, goats, and avian species (e.g. chickens, ducks and geese). Additives of the invention may similarly be used to produce a NORP in livestock feed. That is, a mixture of at least one reducing agent and at least one carrier may be added to animal feeds to enhance the biological value of the feeds. As in other applications where an additive is applied to a dry (i.e. non-aqueous) consumable material, additives may be said to produce a NORP in such materials in that the additives increase the potential for the dry consumable materials to produce an NORP upon being introduced to an aqueous environment.

The additives of the invention may be used to produce a target NORP (and/or pH) for horticultural use. For example, additives may be used to enhance the health of food-producing and ornamental plants. Without being limited to any particular embodiment, the additives of the invention may be used to produce a NORP in aqueous solutions such as water (for hydrating plants), fertilizers, and sprays for use on foliage. Additives of the invention may also be added to soil as a means for increasing the nutrient value (i.e. biological value) of the soil.

The additives of the invention also find use in filtration applications (e.g. water filters) where it is desirable to produce a NORP (and/or increased pH) in a filtered consumable material. Such applications may be practiced using a filter member that is impregnated with, coated with, or manufactured from, an additive comprising at least one reducing agent and at least one carrier. As used herein, the term "filter member" refers to any filter component that contacts a fluid as the fluid passes through a filter device. Filter members include, but are not limited to, porous bodies (e.g. screens or fibrous packing materials) which permit the fluid to flow through them. Filter members may also include solid components such as rods, discs or beads which may be encased in a filter device. Filter members may comprise the wall(s) of a filter device which contacts the filtered fluid. Filter members may be impregnated with, coated with, and/or manufactured from an additive. For example, a filter member may be manufactured from an additive by pressing a dry additive into the shape and form of the filter member.

In a specific, non-limiting method of the invention, drinking water is filtered using a filter device comprising a filter member comprising an additive of the invention. Such methods generally comprise (1) providing a filtering member that is manufactured from, impregnated with, or coated with, an additive, (2) contacting the filtering member with drinking water under conditions suitable to permit the drinking water to achieve a targeted NORP and/or a desired pH, and (3) collecting the filtered drinking water.

Additives for coating, impregnating or manufacturing a filter member have sufficient solubility (i.e. water solubility) to produce a target NORP and/or desired pH in a consumable material as the consumable material flows through, or over, the additive. The additives for coating, impregnating or manufacturing the filter member may further be encapsulated in a polymeric matrix that, releases the additive over time so that the filtering member may be used multiple times while retaining the ability to produce a target NORP and/or increased alkalinity in subsequent applications. Materials for encapsulating the additives of the invention include any polymeric material that can be cross-linked in-situ. Suitable encapsulating materials include, but are not limited to alginates, xantham gum, poly-lactic acid, and the like. Suitable compounds for achieving encapsulation include, but are not limited to, those taught by the following documents, the disclosures of which are incorporated by reference in their entirety: U.S. Pat. Nos. 3,375,933, 6,444,316, 6,527,051, and 7,309,429.

In aspects of the invention, additives may be used to coat the internal surfaces of drinking and food receptacles such as cups, bottles, glasses, bowls, plates, pots, pans, pitchers and the like. Such receptacles produce a NORP in aqueous consumable materials when such materials are contacted with (i.e. placed in) the receptacles. Suitable formulations for such additive coatings are described above. Such coatings may be for a single use and dissolve quickly, or they may be of a time-release nature to permit the receptacle to produce a NORP over multiple uses.

The additives of the invention may be used in wastewater treatment applications. That is, the additives of the invention may be formulated and used to remove contaminants from wastewater. In general terms, such applications are practiced by providing a volume of wastewater, contacting the wastewater with an amount of additive sufficient to produce a level of NORP suitable for causing oxidized contaminants in the wastewater to become reduced and precipitate, and removing the precipitated particles from the wastewater. Precipitated particles may be removed by any method suitable for separating particles from wastewater such as, for example, sedimentation, filtration, centrifugation and the like. Using additives for wastewater treatment may be used to remove any form of oxidized contaminant from wastewater in applications including, but not limited to, municipal and agricultural wastewater treatment. Wastewater treatment as disclosed herein may be practiced with any additive that causes oxidized contaminants in the wastewater to become reduced and precipitate in a manner that permits the particles to be collected and removed. Suitable NORP values for treating wastewater using the additives of the invention include, but are not limited to, NORP in the range of about −50 and −750 mV Some non-limiting, exemplary additives for producing a stabilized NORP are shown in the following examples. Also disclosed are the pH and NORP activities of these exemplary formulations. These examples (and their relative reducing potential and pH) are provided for illustration only and do not in any way limit the additives of the invention to any specific formulation or activity. One skilled in the art will appreciate that these formulations may be modified without departing from the spirit of the invention.

Example 1

| Component | Amount per tablet (mg) | % |
| --- | --- | --- |
| Mg:KHCO$_3$ (1:8) | 300.00 | 60.0% |
| Mannitol | 183.50 | 36.7% |
| PEG 3350 | 15.00 | 3.0% |
| Silica | 1.50 | 0.3% |
| Total | 500.00 | 100.0% |

ORP (for 500 mg tablet/0.5 L water −550 mV
pH = 9.8

Example 2

| Component | Amount per tablet (mg) | % |
| --- | --- | --- |
| Mg:KHCO$_3$ (1:4) | 100.0 | 33.3 |
| KHCO$_3$ | 100.0 | 33.3 |
| Mannitol | 49.0 | 16.3 |
| Malic acid | 50.0 | 16.7 |
| Sodium stearyl fumarate | 1.0 | 0.3 |
| Total | 300.0 | 99.9 |

ORP (for 300 mg tablet/0.5 L water) = −460 mV
pH = 9.6

Example 3

| Component | Amount in g per 100 g of Tableting Powder | % |
| --- | --- | --- |
| KHCO$_3$ (anhydrous) | 57 | 57 |
| NaHCO$_3$ (anh) | 0 | 0 |
| Ca - Lactate × 5H$_2$O | 10 | 10 |
| Inulin (anh) | 9 | 9 |
| Mg (metal −350 mesh) | 8 | 8 |
| Malic Acid (anh) | 8 | 8 |
| L-Leucine anh | 8 | 8 |
| TOTAL (g; %) | 100 | 100 |
| Weight of one tablet | 0.25 g | |

ORP (1 tablet per 0.5 L water) = −690 mV
pH = 10.0

Example 4

| Component | Amount in g per 100 g of Tableting Powder | % |
| --- | --- | --- |
| KHCO$_3$ (anhydrous) | 33 | 33 |
| NaHCO$_3$ (anh) | 17 | 17 |
| Ca - Lactate × 5H$_2$O | 12 | 12 |
| Inulin (anh) | 8 | 9 |

-continued

| Component | Amount in g per 100 g of Tableting Powder | % |
|---|---|---|
| Mg (metal −350 mesh) | 8 | 8 |
| Malic Acid (anh) | 14 | 8 |
| L-Leucine anh | 8 | 8 |
| TOTAL (g; %) | 100 | 100 |
| Weight of one tablet | 0.25 g | |

ORP (1 tablet per 0.5 L water) = −710 mV
pH = 8.5

Example 5

| Component | Amount in g per 100 g of Tableting Powder | % |
|---|---|---|
| $KHCO_3$ (anhydrous) | 33 | 33 |
| $NaHCO_3$ (anh) | 17 | 17 |
| Ca-Lactate × $5H_2O$ | 10 | 10 |
| Inulin (anh) | 8 | 8 |
| Mg (metal −350 mesh) | 8 | 8 |
| Tartaric Acid (anh) | 14 | 14 |
| L-Leucine anh | 10 | 10 |
| TOTAL (g; %) | 100 | 100 |
| Weight of one tablet | 0.25 g | |

ORP (1 tablet per 0.5 L water) = −740 mV
pH = 8.6

Example 6

| Component | Amount in g per 100 g of Tableting Powder | % |
|---|---|---|
| $KHCO_3$ (anhydrous) | 30 | 30 |
| $NaHCO_3$ (anh) | 15 | 15 |
| Ca-Lactate × $5H_2O$ | 10 | 10 |
| Inulin (anh) | 12 | 12 |
| Mg (metal −350 mesh) | 8 | 8 |
| Tartaric Acid (anh) | 15 | 15 |
| L-Leucine anh | 10 | 10 |
| TOTAL (g; %) | 100 | 100 |
| Weight of one tablet | 0.25 g | |

ORP (1 tablet per 0.5 L water) = −630 mV
pH = 8.4

Example 7

Magnesium-Based NORP Formulation

A 600 g NORP producing mixture was formulated as follows:
275 g KHCO3; 45.83%
25 g Mg powder (350 mesh); 4.16%
100 g Ascorbic Acid (AA); 16.66%
(Active ORP part of the formula)
175 g Mannitol; 29.16%
25 g Inulin; 4.16%
One gram of the above mixture was dissolved in one liter of distilled water. After 15 minutes in solution, the mixture produced a NORP of about −300 mV. After standing another 1-2 hours, the mixture produced a NORP of −450 to −550 mV.

Example 8

Preparation of Dihydro-Trigonelline

In the first step, beta-Nicotinic amide (niacin, vitamin B-3) or beta-Nicotinic acid is N-methylated by using a standard methylating agent (such as dimethyl sulfate) using well known procedures in the art to provide high yields of N-methyl derivative (trigonelline—T- and/or the corresponding T-derivatives).

In the second step, the N-methyl derivative is partially reduced according to methods known in the art, preferably using sodium dihydrosulfite to provide 1,4-dihydro-pyridine derivative (dihydro-trigonelline—DHT). This reduced form (DHT) provides a negative ORP when dissolved in aqueous solutions (e.g. water) and depending on the concentration, produces NORP values between about −50 and −300 mV.

Example 9

Preparation of Silica-Boro-Hydride and its Use

Sodium metha-silicate penta-hydrate (MW 212; 50 g) is dissolved in 500 mL of distilled water. Citric Acid (or tartaric acid or malic acid) is added in sufficient quantities to get pH of about 9-10. Upon such acidification, no insoluble silica is visible (we assume that silica stays as a colloidal aqueous solution). To such a solution 5 g of sodium borohydride is added. Mannitol (20 g) is then added and the obtained solution is frozen and lyophilized. The resulting material is a solid white residue of 'silica-boro-hydride' (yield of about 80 g) which can be dissolved in water (50 mg/L) to produce a negative ORP of about −600 mV.

Example 10

NORP Syrup

Approximately 50% of a sugar syrup is made in water using sucrose, glucose, fructose, xylitol, erythritol, or many other edible and GRAS recognized sugars. To such a solution, one adds first a polysaccharide to thicken the sugar syrup (such as apple pectin, xanthan gum and similar) followed by a sufficient amount of (usually about 0.5-1 g) of a $KHCO_3$—Mg (12:1) per liter. Such syrups will be stable for up to 3 months, particularly if kept in refrigerator at +4 C. The ORP of such syrups are usually around −500 mV.

I claim:
1. An edible powder for producing negative oxidation reduction potential (NORP) in foods and other consumable materials, said powder comprising a mixture of
   a) reducing, zero-valent, non-ionic and non-oxidized elemental magnesium metal powder; and
   b) a base selected from magnesium carbonate, sodium carbonate, potassium bicarbonate, sodium carbonate, potassium carbonate, magnesium oxide, calcium carbonate, or a combination thereof;
   c) wherein said elemental magnesium metal and said base are in a ratio of between about 1:4 and 1:50 respectively, and
   d) wherein said reducing, zero-valent, non-ionic and non-oxidized elemental magnesium metal powder comprises particles that are between about 37 to 500 microns in size.

2. The edible powder of claim 1, wherein said edible powder is in the form of a pill, tablet, bead, disc, coating, gain or capsule.

3. The edible powder of claim 1, wherein said base comprises magnesium carbonate.

4. The edible powder of claim 1, further comprising a vitamin, flavoring, coloring, sweetener or combination thereof.

\* \* \* \* \*